(12) United States Patent
Alcuri et al.

(10) Patent No.: US 9,597,715 B2
(45) Date of Patent: Mar. 21, 2017

(54) METHOD FOR PERFORMING WORK ON UNDERWATER PIPES

(71) Applicant: TOTAL SA, Courbevoie (FR)

(72) Inventors: Gustavo Alcuri, Paris (FR); Alexander Somers, Pau (FR); Ann Courbot, Pau (FR); Saïd Ben Chalellou Ouchene, Marseilles (FR)

(73) Assignee: TOTAL SA, Courbevoie (FR)

( * ) Notice: Subject to any disclaimer, the term of this patent is extended or adjusted under 35 U.S.C. 154(b) by 0 days.

(21) Appl. No.: 14/763,066

(22) PCT Filed: Jan. 23, 2014

(86) PCT No.: PCT/FR2014/050134
§ 371 (c)(1),
(2) Date: Jul. 23, 2015

(87) PCT Pub. No.: WO2014/114887
PCT Pub. Date: Jul. 31, 2014

(65) Prior Publication Data
US 2015/0367387 A1    Dec. 24, 2015

(30) Foreign Application Priority Data
Jan. 24, 2013    (FR) .................................... 13 50613

(51) Int. Cl.
*B08B 3/12*    (2006.01)
*G01N 17/00*    (2006.01)
(Continued)

(52) U.S. Cl.
CPC ................ *B08B 3/12* (2013.01); *B08B 9/027* (2013.01); *B08B 9/0321* (2013.01); *F16L 1/26* (2013.01);
(Continued)

(58) Field of Classification Search
CPC ...................................... G01F 1/66; E03C 1/30
(Continued)

(56) References Cited

U.S. PATENT DOCUMENTS 3,175,567 A    3/1965    Crawford
3,489,434 A *  1/1970    Frank .................. F16L 37/1205
                                                            285/1

(Continued)

FOREIGN PATENT DOCUMENTS

FR    2 754 898 A1    4/1998
GB    2 440 948 A      2/2008
(Continued)

OTHER PUBLICATIONS

PCT International Search Report and Written Opinion for PCT/FR2014/050134, mailed May 6, 2014, 10 pgs.
(Continued)

*Primary Examiner* — Sean Andrish
(74) *Attorney, Agent, or Firm* — Patterson Thuente Pedersen, P.A.

(57) ABSTRACT

An apparatus for underwater pipes comprising an ultrasound emitting system and at least one ultrasound receiving transducer is lowered into he marine environment. During an inspection phase, an ultrasound inspection source of the ultrasound emitting system and the receiving transducer are disposed on each side of the pipe. The inspection source is activated, and an ultrasound signal captured by the receiving transducer is recorded. In response to the observation of an anomaly in the ultrasound signal captured by the receiving transducer, a power source of the ultrasound emitting system is then coupled to the pipe at the aforementioned location, and the power source is activated in order to destroy the obstruction.

12 Claims, 6 Drawing Sheets

(51) Int. Cl.
*B08B 9/032* (2006.01)
*B08B 9/027* (2006.01)
*F16L 1/26* (2006.01)
*G01N 29/04* (2006.01)
*F28G 7/00* (2006.01)

(52) U.S. Cl.
CPC ......... *G01N 17/008* (2013.01); *G01N 29/043* (2013.01); *B08B 2209/005* (2013.01); *F28G 7/00* (2013.01); *G01N 2291/044* (2013.01); *G01N 2291/2634* (2013.01)

(58) Field of Classification Search
USPC ................................ 405/184.1; 134/1, 22.11
See application file for complete search history.

(56) References Cited

U.S. PATENT DOCUMENTS

| | | | | |
|---|---|---|---|---|
| 4,565,088 A | * | 1/1986 | Crambes | G01N 29/024 73/290 V |
| 4,893,361 A | | 1/1990 | Burns | |
| 2005/0284625 A1 | | 12/2005 | Rodney et al. | |
| 2008/0215248 A1 | | 9/2008 | Magalhaes Mendes et al. | |
| 2009/0078049 A1 | * | 3/2009 | Sinha | G01N 29/02 73/623 |
| 2011/0303012 A1 | * | 12/2011 | Amundsen | G01B 7/066 73/579 |
| 2013/0298937 A1 | * | 11/2013 | O'Donnell | E03C 1/30 134/1 |

FOREIGN PATENT DOCUMENTS

| | | |
|---|---|---|
| RU | 2378058 C1 | 1/2010 |
| WO | WO 2010/086238 A1 | 8/2010 |

OTHER PUBLICATIONS

English translation of PCT International Search Report for PCT/FR201/050134 mailed May 6, 2014, 3 pages.
English translation of Office Action from Kazakhstan Application No. 2015/0964.4, dated Nov. 4, 2016, 3 pgs.

\* cited by examiner

METHOD FOR PERFORMING WORK ON UNDERWATER PIPES

RELATED APPLICATIONS

The present application is a National Phase entry of PCT Application No. PCT/FR2014/050134, filed Jan. 23, 2014, which claims priority from FR Patent Application No. 13 50613, filed Jan. 24, 2013, said applications being hereby incorporated by reference herein in their entirety.

FIELD OF THE INVENTION

This invention relates to offshore techniques and in particular techniques implemented to detect, locate, characterise and/or destroy obstructions in underwater pipes, in particular in the context of the offshore production of hydrocarbons.

BACKGROUND OF THE INVENTION

The pipes that are of interest here include any hydrocarbon duct located between a well-head (on the sea floor) and a boat intended for the storage and possibly the treatment of hydrocarbons, commonly referred to as FPSO (floating production, storage and offloading). These ducts include in particular the production lines (flowline), jumpers, spools, risers and bundles.

On the other hand, obstruction means any type of solid deposit or deposit with substantial viscosity able to be located inside the pipe, and therefore able to hinder the flow of the hydrocarbons. This can be deposits of hydrates, paraffins, minerals, asphaltenes and naphtenates. In particular, clogs formed of gas hydrate crystals can form in pipes for transporting hydrocarbons. These hydrates are formed in the presence of light hydrocarbon gases (methane, ethane, propane, etc.) and of water molecules in conditions of high pressure and low temperature. Such conditions come together in particular in the case of underwater pipes used in offshore oil and gas operations.

Of course, the appearance of obstructing elements in offshore pipes is highly undesirable. If the obstruction is partial, i.e. if it does not close the entire section of the pipe, it substantially disturbs the flow, all the more so that the formation of hydrates or of other compounds also tends to increase the viscosity of the fluid to be transported. If the obstruction is total, the pipe is completely out of service. When such circumstances arise, the operator needs effective techniques to locate where the obstruction is along the pipe and in order to destroy it. It is in particular desirable that these techniques not be intrusive, i.e. do not require opening the pipe in order to access the inside.

A known method for attacking clogs of hydrates uses a depressurisation of the pipe in order to break the thermodynamic equilibrium that favours the formation of hydrates. The depressurisation has to be obtained simultaneously on both sides of the clog, in order to balance the mechanical effect on the latter and as such prevent the clog from moving too abruptly in the pipe rather than be destroyed. This operation is not always possible, in particular in the case of multiple clogs or in the case of a partial obstruction.

The injection of chemical inhibitors can be an additional means of provoking the phenomenon of dilaceration. Commonly used agents are, for example, ethanol or methanol. They must be injected in large quantities.

Another approach is based on the action of power ultrasound transducers distributed around the pipe. GB 2440 948 A mentions removing obstructions on the inner wall of a pipe by means of ultrasound transducers distributed around the pipe and by applying multi-frequency vibrations in order to generate cavitation bubbles able to pull off elements that are obstructing the pipe.

Before attacking a clog in a pipe, it has to be able to be located. Preferably, the locating method used must be non-intrusive, i.e. not require access to the inside of the pipe, which may be impossible or highly inconvenient, especially in the deep offshore.

Known methods for detecting deposits in a pipe use a vibratory excitation generated by an actuator which provokes a response measured on a sensor located downstream of the actuator along the pipe. US 2008/0215248 A1 describes such a method for detecting bio-films that can be depositing on the walls of reservoirs or pipes that are part of industrial installations. In WO 2010/086238 A1, it is proposed to estimate the thickness of a waxy deposit inside oil pipelines by a measurement of the resonance frequency of the structure. The method described in FR 2754898 B1 seeks to evaluate the thickness of the deposit possibly formed inside the pipe using an estimation of the low-frequency vibration attenuation coefficients (less than 5 kHz) in the excited portion of the pipe.

These various methods can be delicate to implement. They do not provide a global response to the problem of locating and of destroying obstructions in offshore pipes.

There is a need for an approach that is better suited to the underwater environment.

SUMMARY OF THE INVENTION

The invention proposes a method for performing work on an underwater pipe, comprising a phase of lowering into the marine environment an apparatus comprising an ultrasound emitting system and at least one ultrasound receiving transducer, an inspection phase along the pipe using the lowered apparatus then, when the inspection phase shows a condition for locating an obstruction at a location along the pipe, a destruction phase of the obstruction at this location using the lowered apparatus.

The inspection phase comprises:
  arranging an ultrasound inspection source of the ultrasound emitting system and the receiving transducer on either side of the pipe;
  activating the inspection source and recording an ultrasound signal captured by the receiving transducer; and
  detecting the condition for locating an obstruction at the location wherein are arranged the inspection source and the receiving transducer in response to the observation of an anomaly in the ultrasound signal captured by the receiving transducer at this location.

The destruction phase comprises:
  coupling a power source of the ultrasound emitting system to the pipe at said location; and
  activating the power source in order to destroy the obstruction.

The same apparatus is therefore used to locate and then to destroy, or at least attempt to destroy, an obstruction as soon as it has been located. An ultrasound excitation is used in both cases. The terms "ultrasound inspection source" and "power source" each designate an ultrasound wave emitting device, which can for example be a transducer.

In a particular embodiment, the method further comprises a verification phase wherein the inspection source and the receiving transducer are again arranged on either side of the pipe after the destruction phase of the obstruction, and the inspection source is activated in order to verify if the ultrasound signal captured by the receiving transducer still has the anomaly.

The apparatus is advantageously displaced along the pipe during the inspection phase, and the step of activating the inspection source and of recording the ultrasound signal captured by the receiving transducer is repeated until an anomaly is observed in the ultrasound recorded signal, which gives the presumed position of an obstruction.

The ultrasound excitation is typically at a higher frequency in the inspection phase than in the destruction phase. In particular, the inspection source can be activated in pulse mode in the inspection phase. The anomaly can then be observed in the spectrum of the signal captured by the receiving transducer, most often in the highest frequencies of this spectrum.

In the destruction phase, the power source is advantageously activated by a wideband control signal. This can in particular be a substantially monochromatic control signal of which the ultrasonic frequency is varied. The wideband scanned during the frequency variation can be a range between 10 kHz and 30 kHz. The ultrasonic frequency of the substantially monochromatic control signal can vary in this range with a scanning frequency less than 500 Hz. It is as such ensured that the frequency of the signal for attacking the obstruction has the opportunity to coincide repetitively with the resonance frequency of the system formed by the pipe and the obstruction that it contains, as such maximising the transfer of power from the power source to the target.

Note that the mechanical response to the excitation of the pipe-obstruction system varies as the destruction process unfolds given that the size, shape and/or physical-chemical nature of the obstruction changes. The frequency scanning nevertheless makes it possible to reach the obstruction without it being necessary to precisely know the change in its size, its shape or its physical-chemical nature.

During the destruction, the effect of the direct mechanical excitation of the obstruction is combined with that of the attack via the cavitation phenomenon which can take place in light of the presence of a liquid medium in the pipe.

BRIEF DESCRIPTION OF THE DRAWINGS

Other particularities and advantages of this invention shall appear in the description hereinafter of an unrestricted embodiment, in reference to the annexed drawings, wherein.

DETAILED DESCRIPTION OF THE DRAWINGS

The apparatus used in the method proposed here comprises an ultrasound emitting system that can produce an excitation applied to the underwater pipe 100 resting on the seafloor with the help of supports 101. This excitation is either a pulse, or is monochromatic with a variable frequency.

Figure 1:
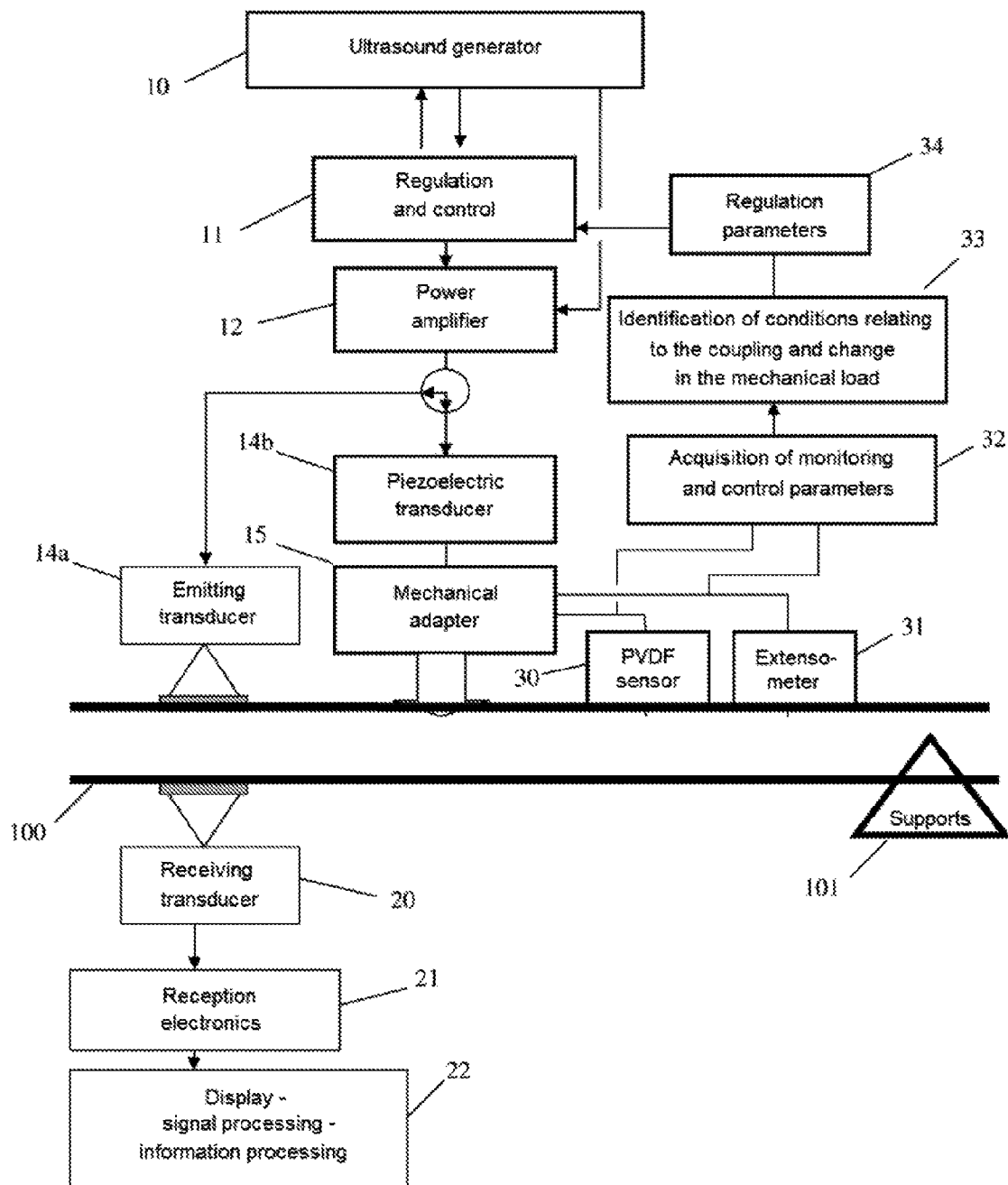
FIG. 1 is a block diagram of an apparatus for locating and destroying obstructions in underwater pipes according to a first embodiment that uses only one ultrasound generator and dissociated piezoelectric transducers.

In the example shown in FIG. 1, these two types of excitation are produced using an ultrasound generator 10 that cooperates with a regulation and control unit 11. The ultrasound signal coming from the generator 10 is amplified by the amplifier 12, to a level of power that is suited for the operation in progress, then is directed either to an emitting transducer 14a (for an inspection phase) or to a power transducer 14b (for a destruction phase). A mechanical adapter 15 in contact with the pipe 100 carries out the coupling between the power transducer 14b and the pipe 100. In the example of FIG. 1, the inspection source and the power source used in the destruction phase share the ultrasound generator 10.

Figure 2:
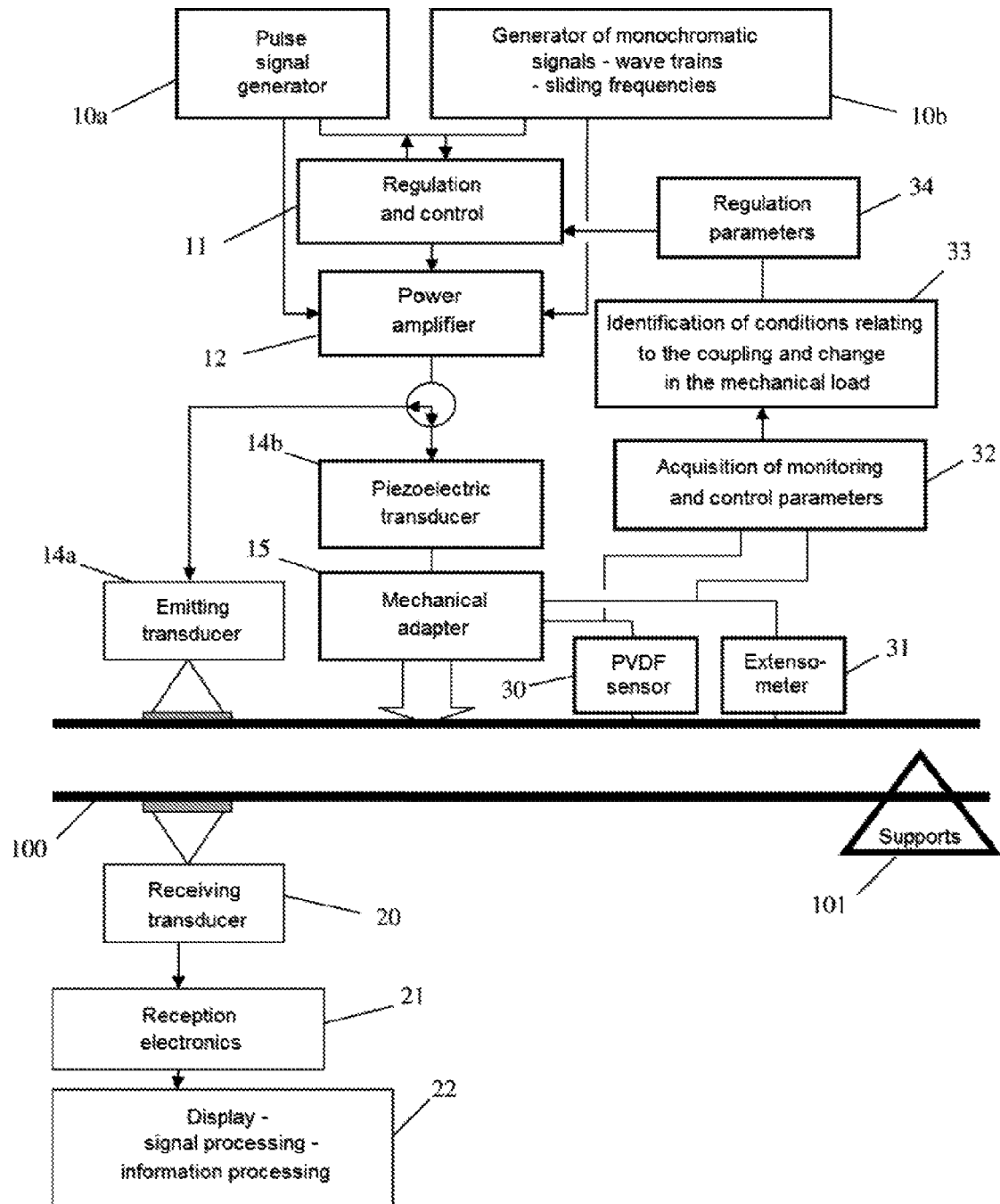
FIG. 2 is a block diagram of an apparatus for locating and destroying obstructions according to a second embodiment wherein the ultrasound sources (generator + piezoelectric transducer) are dissociated.

In an alternative shown in FIG. 2, the ultrasound emitting system has two separate sources. The inspection source comprises a pulse signal generator 10a and the emitting transducer 14a receiving the amplified signals from this generator 10a. For the destruction, the power source comprises a monochromatic signal generator 10b in the form of sliding frequency wave trains and the power transducer 14b.

Figure 3:
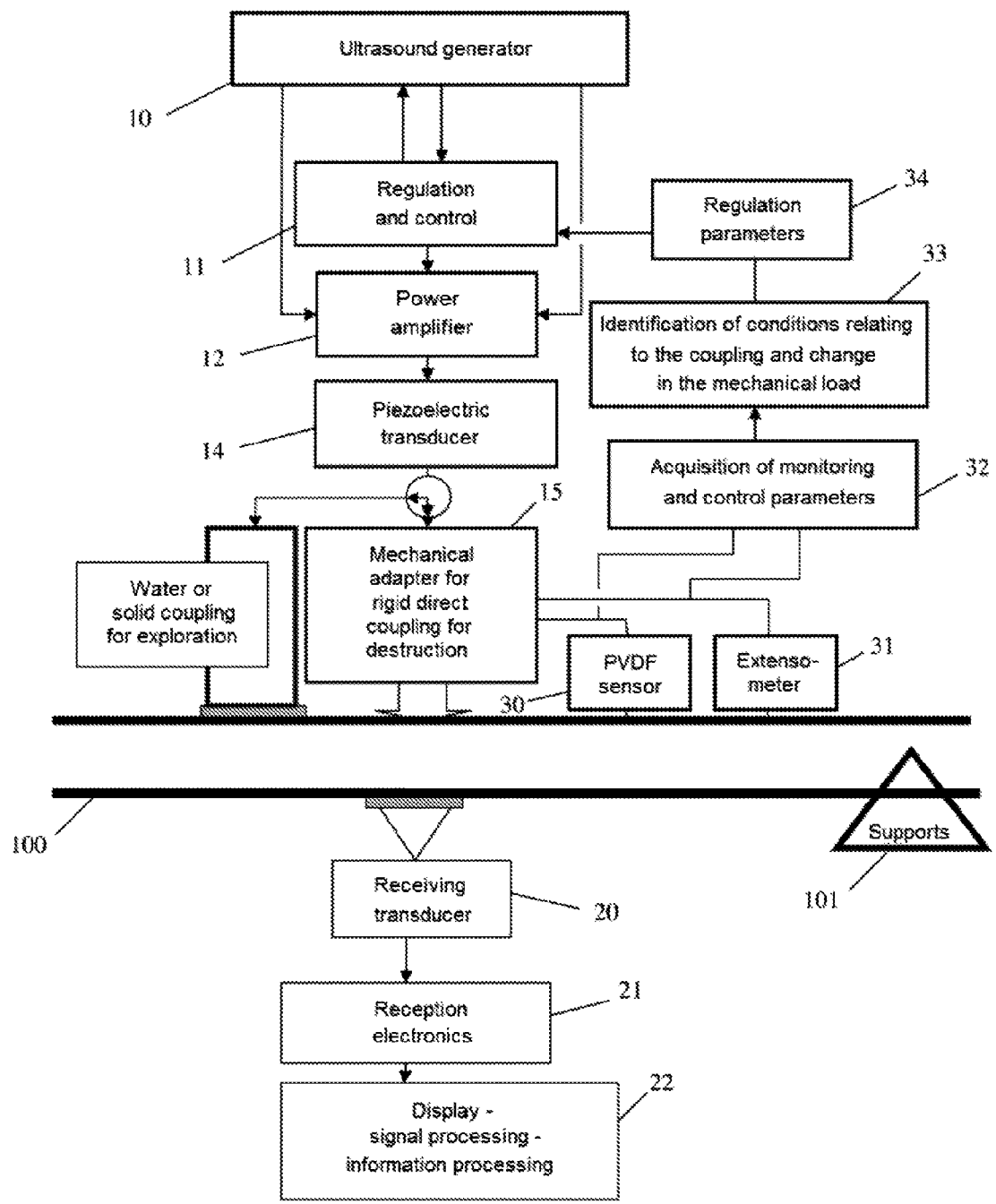
FIG. 3 is a block diagram of another apparatus according to a third embodiment that uses a single ultrasound source in inspection phase and in destruction phase.

In another alternative shown in FIG. 3, the inspection source and the power source share the same ultrasound generator 10 and the same transducer 14.

The apparatus further comprises one or several ultrasound receiving transducers 20 used in the inspection phase. A reception electronics 21 receives the ultrasound signals captured by this or these transducers 20 in order to amplify them, format them and supply them to a visualisation and processing unit 22. In an advantageous configuration, there is a receiving transducer 20 placed diametrically opposite the emitting transducer 14a with respect to the pipe 100.

In an embodiment according to FIG. 1 or FIG. 2, the control electronics are connected to two separate piezoelectric transducers, with one 14a operating for locating obstructions, the other 14b for the destruction. Each transducer can as such be optimised for the function that it must fulfil. The emitting transducer 14a can in particular comprise means that make it possible to facilitate its displacement along the pipe 100. Indeed, during the inspection phase, mobility of the system needs to be provided along the pipe. Inversely, in the destruction phase, an optimal coupling is sought between the transducer and the pipe, in order to provide an optimised transfer of energy to a determined point. The transducer 14b can as such advantageously comprise rigid means of fastening.

In a particular embodiment (FIG. 1 or FIG. 3), the ultrasound generator 10 is able to generate both wideband pulse signals and variable frequency monochromatic signals. In order to detect any obstructions in the pipes it is desirable to use wideband pulse signals, while the variable frequency monochromatic signals make it possible to carry out the destruction of the obstructions detected at a given location.

The frequency characteristics of the signals arriving at the structure to be inspected are determined by the product of the signal output by the generator 10, 10a and the response of the emitting transducer 14a. When this complex signal passes, the structure will provide the receiving transducer 20 with a multi-frequency response, which leads to the obtaining of a spectral signature according to the physical situation of the target: absence of a deposit, presence of a deposit, etc.

Signals of the pulse type are characterised by a wide spectrum content. In order to obtain an appropriate spectral signature, it is therefore preferable to use this type of signal.

Inversely, the destruction function is better served by signals of the monochromatic type, which carry a high energy level.

The adaptation of the frequency to a certain physical-chemical situation of the target, which necessarily changes in a process of destruction, is obtained thanks to the use of an excitation with sliding frequencies. The scanning frequency rate, in an interval that depends on the response of the transducer 14b, is substantially faster than the time for establishing mechanical actions and induced cavitation.

In a particular embodiment, each signal generator can be associated with control electronics and with a separate piezoelectric transducer, with one of the transducers operating for locating obstructions and the other transducer operating for destroying obstructions, with each transducer as such optimised for the function that it must fulfil. The unit comprised of the pulse signal generator, the control electronics and the emitting piezoelectric transducer is referred to as the pulse source.

In a particular embodiment, a feedback loop makes it possible to verify the coupling between the apparatus and the pipe, and possibly to reposition the mechanical adapter 15 in order to optimise the coupling. This feedback loop, shown on the right-hand side of FIGS. 1-4, typically comprises a PVDF sensor 30 (polyvinylidene fluoride) and an extensometer 31 coupled to an electronic unit for the acquisition of monitoring and control parameters 32. These parameters are supplied to an analysis unit 33 that identifies the conditions relating to the coupling and to the changes of the mechanical load felt by the ultrasound system. The analysis unit 33 then generates the regulation parameters 34 which are applied to the regulation and control unit 11 in order to control the process of the destruction of obstructions.

The apparatus is installed on a ROV (remotely operated vehicle) or an AUV (autonomous underwater vehicle), in order to be lowered and controlled in the marine environment from a vessel or a platform located on the surface, in order to perform work on an underwater pipe 100. The work on the pipe can be performed during a routine control operation, or after detection, on the surface, of a disturbance in the flow imputed to an obstructing element located inside the pipe, such as for example a clog of hydrates.

After lowering the apparatus into the marine environment, and positioning the latter on the pipe, a first phase of the work consists in locating the presumed obstruction. This inspection phase uses the pulse source (10, 14a in FIG. 1/10a, 14a in FIG. 2/10, 14 in FIG. 3/10a, 14a in FIG. 5) and the receiving ultrasound transducer or transducers 20.

Figure 5:
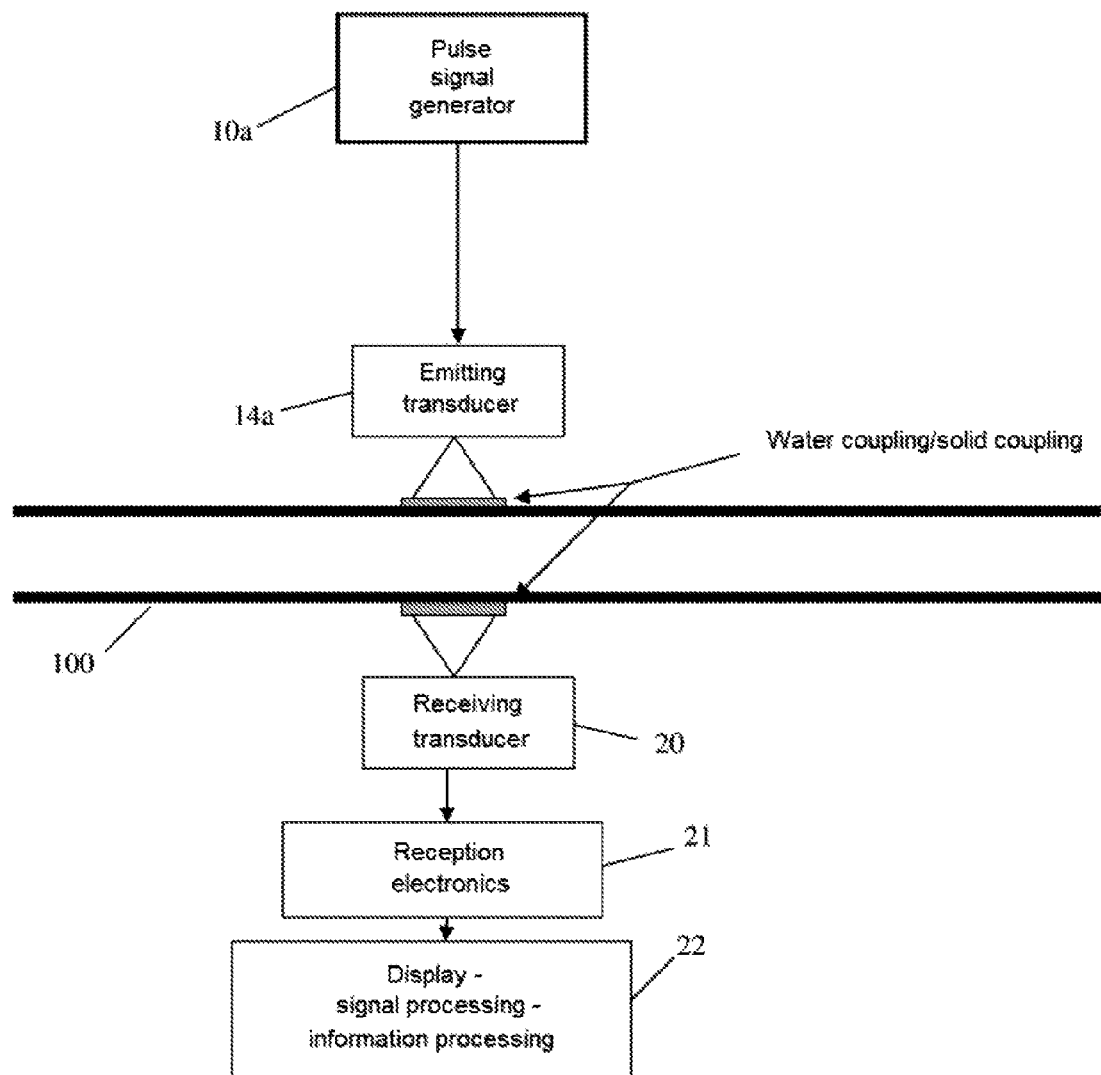
FIG. 5 is a block diagram of a system for locating obstructions.

FIG. 5 shows a possible positioning of the pulse source and of a receiving ultrasound transducer 20 in the inspection phase, in one of the embodiments shown in FIGS. 1-3. The pulse source comprises the generator 10, 10a of wideband pulse signals associated with the emitting transducer 20. The emitting transducer 14a is of the piezoelectric type, comprised of a stack of ceramics associated with a distribution part. The geometry and the structure of this distribution part are suited to obtain good directivity of the source towards the inspected pipe.

The emitting transducer 14, 14a and the receiving transducer 20 are placed on either side of the pipe 100. As such, the ultrasound waves captured by the transducer 20 are waves that have been transmitted from the transducer 14a through a medium comprising, in addition to seawater, the pipe 100 and possibly an obstruction contained in this pipe.

Figure 6:
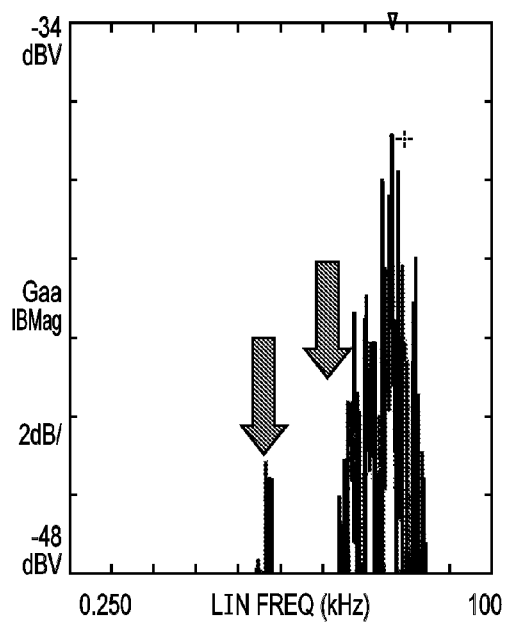
FIGS. 6 and 7 are figures that show examples of ultrasound spectra recorded by a receiving transducer in a locating phase.
Figure 7:
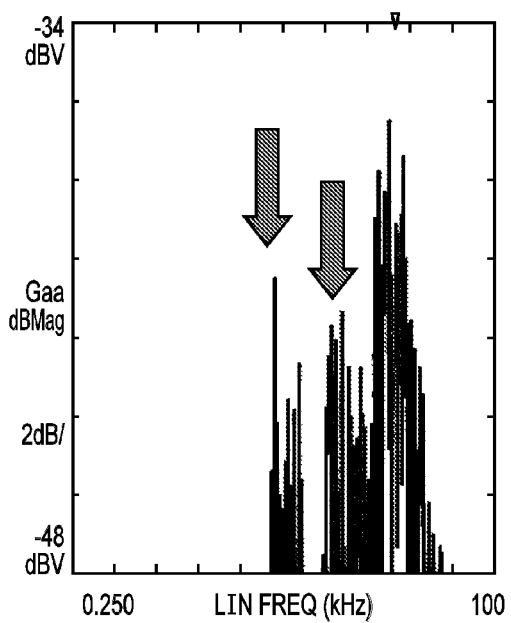

The processing unit 22 associated with the receiving transducer 20 makes it possible to record and analyse a spectral signal. As shown in FIGS. 6 and 7, the spectral signal has a different form according to whether the pipe 100 is simply filled with liquid, or that it has an obstructing element at the location where the emitting 14, 14a and receiving 20 transducers are arranged.

By comparing spectral signals, it is possible to identify and locate a possible obstruction. This operation is carried out automatically by the processing unit 22.

The apparatus is displaced along the pipe 100, using the ROV/AUV, in order to successively position the pulse source 14a and the receiving transducer 20 at different locations along the pipe. At each location, a spectral signature is recorded by the processing unit 22. A first spectral signature is generally observed as long as the pipe 100 contains liquid (for example according to FIG. 6). As soon as an obstruction is encountered, a second spectral signature (for example according to FIG. 7), that differs from the first is recorded by the processing unit 22, and is detected as an anomaly. An obstruction is as such located in the pipe 100 at the location under consideration, without having needed to access the inside of the pipe.

Once an obstruction has been located in the inspection phase, a destruction phase is carried out at this location.

Figure 4:
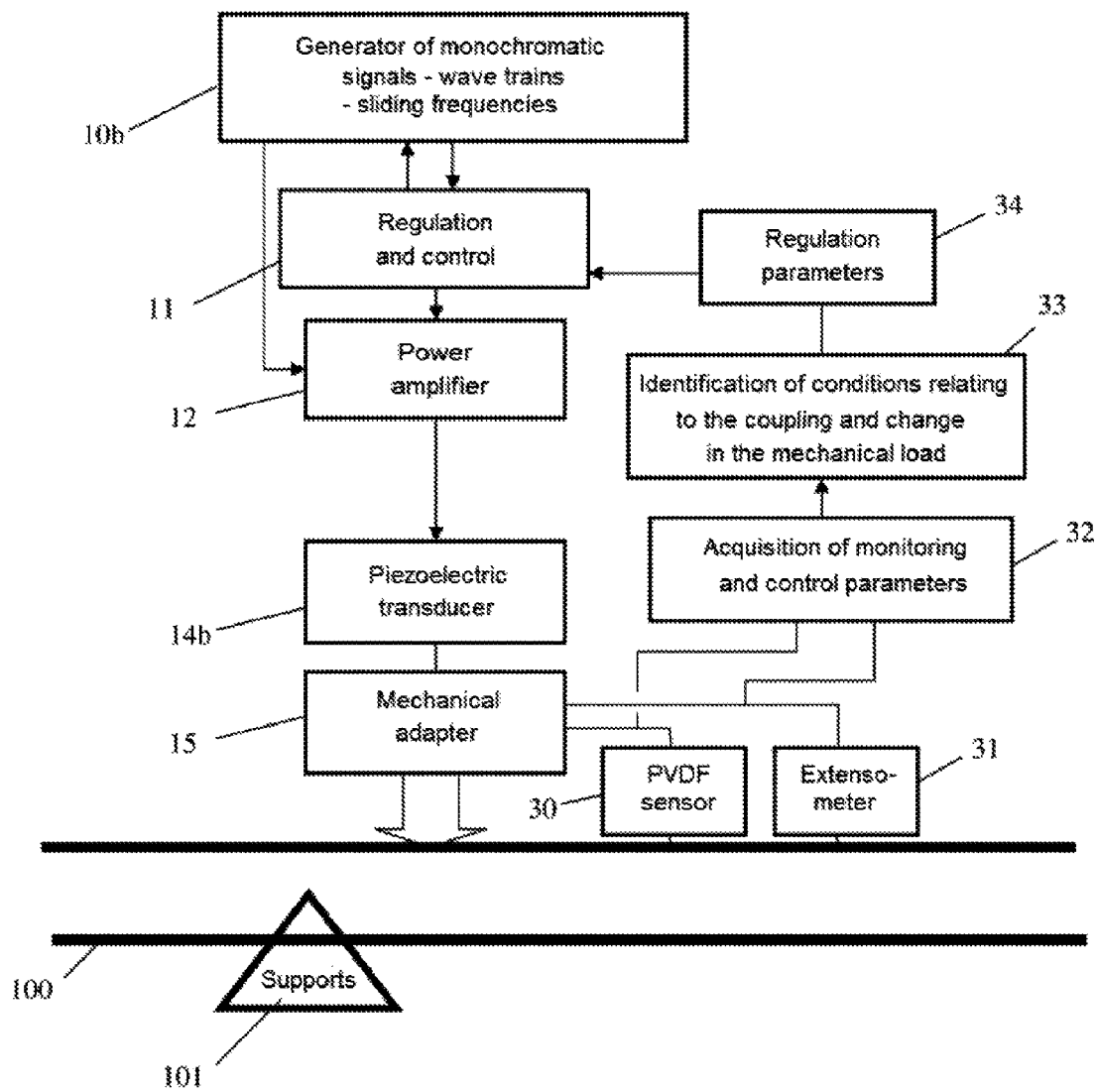
FIG. 4 is a block diagram of a system for destroying obstructions.

The system shown diagrammatically in FIG. 4 can be used for this purpose, in one of the embodiments shown in FIGS. 1-3. This system comprises an ultrasound source that comprises a transducer 14b associated with a variable frequency monochromatic signal generator 10b. The transducer 14, 14b is comprised of a stack of piezoelectric ceramics separated by metal polarisation parts to which the power signals coming from the generator 10, 10b and amplified by the amplifier 12 are applied.

In the destruction phase, the power source is activated in a range of ultrasonic frequencies that is lower than the inspection source in the inspection phase. The range of ultrasonic frequencies in the destruction phase can in particular be between 10 kHz and 30 kHz.

The transducer 14b transforms the electrical excitation into a high-frequency piston movement which attacks the pipe 100 via the mechanical adapter 15 which carries out the coupling. The transducer module 14b can be comprised of several units organised in a star configuration around the pipe 100. The excitation of these multiple units can come from amplifiers that are respectively dedicated to them, or from the same amplifier 12 the output signals of which are distributed using an additional module for programming excitation cycles.

The adapter 15 provides the transfer of energy from the transducer 14, 14b to the pipe 100. The quality of the coupling plays a major role in the capacity of the system to act on the obstruction. In order to provide for this, specific sensors are installed in the vicinity of the adapter 15 in order to obtain information on the quality of the mechanical coupling and to adjust the adapter 15. These specific sensors include the PVDF sensor 30 and the extensometer 31 which measure the mechanical response of the pipe 100 to the ultrasound excitation and supply their results to the acquisition unit 32 and the analysis unit 33.

In a calibration phase of the system, values concerning the force and the output voltage from the PVDF sensors are obtained in conditions of direct monitoring of operations. These values are structured in the form of databases that integrate: the clamping conditions, the geometric characteristics of the pipe, the structural characteristics of the pipe, the nature of the insulation around the pipe, the structure of this insulation, the definition and the characteristics of the multiphase system circulating in the pipe, the nature of the obstruction, the structural characteristics of the obstruction, the output data from the extensometer 31, the output data from the PVDF sensor 30.

The databases are processed using neural structures of the formal neural network type or advanced information processing methods of the SVM type for example ("Support Vector Machines"). Comparing the laboratory results with the data collected in the field makes it possible to monitor the installation conditions of the system for destroying obstructions, and to verify the quality of the coupling. It leads to the decision to start the destruction operations.

Simultaneously, the data supplied by the sensors 31 provide information on the change in the process of destruction. Indeed, the global result of the in situ measurements is according to the response of the structure, as a whole, therefore in relation with the load represented by the obstruction and the change in the load derived from the transformation of the structure (disaggregation of the obstruction).

The action on the obstruction is comprised of two main factors:
the vibrations directly induced in the structure provoking mechanical constraints in the obstruction;
the phenomena of cavitation, responsible for violent aggressions in pressure and temperature on the surface of the obstruction in contact with the liquid where the cavitation is produced.

The fractures generated in the obstruction by the high-frequency vibratory action can be filled by the liquid, which makes it possible to obtain the action of cavitation inside the obstruction. The surfaces attacked by the cavitation are multiplied and the effectiveness of the desegregation process is globalised.

Detecting and evaluating the action of cavitation constitutes an additional control element, in association with the obtaining of vibratory data. The measurements taken by the sensors, associated with electronic modules for acquisition, processing, selective filtering and thresholding, lead to the detecting and evaluating of the action of cavitation by a non-intrusive method.

In the destruction phase of an obstruction, the control signal coming from the generator 10, 10b is advantageously a monochromatic signal the frequency of which varies within the wideband explored, for example from 10 to 30 kHz. The regulation and control unit 11 scans the ultrasonic frequency of this monochromatic signal (or narrowband) during repetitive cycles which make it possible to maximise the probability of encountering a resonance frequency of the pipe–obstruction system in the current state of the obstruction. The scanning frequency in these cycles is typically less than 500 Hz.

Once the destruction phase of an obstruction has been carried out during a determined period of time or following a change detected by the sensors the system for locating (FIG. 4) can be put back into place at the current location of the apparatus, in order to verify if the anomaly of the spectrum of the signal obtained by supplying the emitting transducer 14, 14a of the inspection source is still present. This verification phase makes it possible to identify if the obstruction is still present at the location under consideration along the pipe 100. If it is still present, the destruction phase can be continued.

The embodiments described hereinabove are illustrations of this invention. Various modifications can be made to them without leaving the scope of the invention which stems from the annexed claims.

The invention claimed is:

1. A method for performing work on an underwater pipe, comprising a phase of lowering into the marine environment an apparatus comprising an ultrasound emitting system and at least one ultrasound receiving transducer, an inspection phase along the pipe using the lowered apparatus then, upon detecting a condition for locating an obstruction at a location along the pipe in the inspection phase, a destruction phase of the obstruction at said location using the lowered apparatus,
the inspection phase comprising:
arranging an ultrasound inspection source of the ultrasound emitting system and the at least one ultrasound receiving transducer on either side of the pipe;
activating the ultrasound inspection source and recording an ultrasound signal captured by the at least one ultrasound receiving transducer; and
detecting the condition for locating the obstruction at the location along the pipe wherein are arranged the inspection source and the at least one ultrasound receiving transducer in response to the observation of an anomaly in the ultrasound signal captured by the at least one ultrasound receiving transducer at the location,
and the destruction phase comprising:
coupling a power source of the ultrasound emitting system to the pipe at said location; and
activating the power source in order to destroy the obstruction,
the power source in the destruction phase being activated in a range of ultrasonic frequencies that is lower than a range of ultrasonic frequencies of the ultrasound inspection source in the inspection phase.

2. The method of claim 1, further comprising, in the inspection phase:
displacing the apparatus along the pipe, and
repeatedly activating the ultrasound inspection source and recording the ultrasound signal captured by the at least one ultrasound receiving transducer until an anomaly is observed in the ultrasound signal recorded.

3. The method of claim 1, further comprising, in the inspection phase:
activating the ultrasound inspection source in pulse mode.

4. The method of claim 3, further comprising, in the inspection phase:
analysing the spectrum of the signal captured by the at least one ultrasound receiving transducer in order to detect said anomaly in the spectrum.

5. The method of claim 1, wherein the power source and the inspection source use the same ultrasound emitting transducer.

6. The method of claim 1, further comprising, in the destruction phase:
activating the power source by a wideband control signal.

7. The method of claim 6, wherein the wideband is a range of ultrasonic frequencies between 10 kHz and 30 kHz.

8. The method according to claim 6, wherein the control signal is substantially monochromatic, with an ultrasonic frequency varying over time.

9. The method according to claim 8, further comprising:
scanning the wideband with a scanning frequency less than 500 Hz using the ultrasonic frequency of the substantially monochromatic control signal.

10. The method of claim 1, further comprising, in the destruction phase:
   verifying the coupling with the pipe using a force sensor associated with the power source.

11. The method of claim 1, further comprising, after the destruction phase of the obstruction in said location, a verification phase comprising:
   arranging the ultrasound inspection source and the at least one ultrasound receiving transducer again on either side of the pipe and
   activating the ultrasound inspection source in order to verify whether the ultrasound signal captured by the at least one ultrasound receiving transducer still has the anomaly.

12. The method according to claim 7, wherein the control signal is substantially monochromatic, with an ultrasonic frequency varying over time.

\* \* \* \* \*